(12) United States Patent
Wiener et al.

(10) Patent No.: US 8,580,318 B2
(45) Date of Patent: Nov. 12, 2013

(54) NATURAL WATER SOLUBLE EXTRACTS FOR THE INHIBITION OF ALPHA-1-ADRENERGIC RECEPTORS

(75) Inventors: Harold Wiener, Jerusalem (IL); Avi Gal, Haifa (IL); Irena Oleinik, Ma'alot (IL); Irena Paluy, Kibbutz Dafna (IL); Emma Kvitnitsky, Kiriat Shemona (IL); Tzvia Shapira, Ramat-hasharon (IL)

(73) Assignee: Naturamed Ltd., Jerusalem (IL)

( * ) Notice: Subject to any disclaimer, the term of this patent is extended or adjusted under 35 U.S.C. 154(b) by 825 days.

(21) Appl. No.: 12/585,968

(22) Filed: Sep. 29, 2009

(65) Prior Publication Data

US 2010/0092586 A1   Apr. 15, 2010

Related U.S. Application Data

(63) Continuation-in-part of application No. PCT/IL2008/000444, filed on Mar. 30, 2008.

(30) Foreign Application Priority Data

Mar. 29, 2007   (IL) .......................................... 182284

(51) Int. Cl.
*A61K 36/00* (2006.01)
(52) U.S. Cl.
USPC ......................................................... 424/725
(58) Field of Classification Search
None
See application file for complete search history.

(56) References Cited

U.S. PATENT DOCUMENTS

2007/0134355 A1 *  6/2007  Noldner et al. ............... 424/767

FOREIGN PATENT DOCUMENTS

WO   WO 2005/041994   5/2005

OTHER PUBLICATIONS

Viable Herbal Solutions (www.web.archive.org/web/20000241 13832/http:/viable-herbal.com/herbology1/herbs42.htm, copyrighted 1996,1997,1998 and 2000).*
International Search Report for PCT/IL2008/000444, mailed Sep. 2, 2008.
Written Opinion of the International Searching Authority for PCT/IL2008/000444, mailed Sep. 2, 2008.
Jonas, A et al., "Cactus Flower Extracts may Prove Beneficial in Benign Prostatic Hyperplasia Due to Inhibition of 5 Alpha Reductase Activity, Aromatase Activity and Lipid Peroxidation", Urological Research, vol. 26, No. 4, (Jan. 1, 1998), pp. 265-270.
Palevitch, D et al., "Treatment of Benign Prostatic Hypertrophy with *Opuntia Ficus-Indica* (L.) Miller" Journal of Herbs, Spices, Medicinal Plants, vol. 2, No. 1, (1993), pp. 45-49.
European Patent Office Abstract, & JP 10-059995 (Mar. 3, 1998).
Chapple, C. R., "Pharmacological Therapy of Benign Prostatic Hypeplasia/Lower Urinary Tract Symptoms: An Overview for the Practising Clinician", BJU International, vol. 94, No. 5, (Sep. 2004), pp. 738-744.
Lowe, F. C., "Phytotherapy in the Management of Benign Prostatic Hyperplasia", Urology, vol. 58, No. 6, (Dec. 2001), pp. 71-77.

* cited by examiner

*Primary Examiner* — Terry McKelvey
*Assistant Examiner* — Randall Winston
(74) *Attorney, Agent, or Firm* — Nixon & Vanderhye PC

(57) ABSTRACT

The present invention discloses therapeutic natural products, in particular plant extracts effective in treating and preventing urinary tract disorders, and method for obtaining said extracts. In particular, the present invention discloses a water-soluble alcoholic extract of *Opuntia ficus-indica* flower (NABIA extract), a component thereof (NABIA fraction) or any mixture of components thereof, which is substantially free of non water-soluble residues, and exhibits an effective alpha-1-adrenergic receptor blocking activity. Further are disclosed methods of preparing this extract and methods of inhibiting alpha-1-adrenergic receptors and/or 5-alpha-reductase, as well as of treating medical conditions associated therewith, such as urinary tract disorders.

19 Claims, 2 Drawing Sheets

NATURAL WATER SOLUBLE EXTRACTS FOR THE INHIBITION OF ALPHA-1-ADRENERGIC RECEPTORS

This application is a Continuation-In-Part of International Application No. PCT/IL2008/00044, filed 30 Mar. 2008, which designated the U.S. and claims the benefit of IL 182284, filed 29 Mar. 2007, the entire contents of which is hereby incorporated by reference.

Urinary tract disorders, particularly benign prostatic hyperplasia (BPH) affect a relatively large percentage of males over the age of 50, and is observed in approximately 70% of males over the age of 70.

BPH is a progressive condition, which results in a range of lower urinary tract symptoms (LUTS), which include increased frequency of urination, nocturia, a weak urine stream, hesitancy or delay in starting the urine flow and incomplete bladder emptying. Chronic consequences of BPH can include hypertrophy of bladder smooth muscle, a decompensated bladder, an increased incidence of urinary tract infection, urinary stone formation and renal failure. It is noted that women can also develop LUTS due to unstable bladder contractions.

This disorder is heterogeneous and may be caused by hormonal factors, growth factors, stromal-epithelial interactions, and aging.

Treatment options for BPH include lifestyle modification, device, surgery, pharmacologic, and phytotherapeutic interventions. Until recently, the risks of untreated BPH were difficult to define. However, epidemiologic data now demonstrate a clear correlation between prostate size and risks.

There are two classes of pharmacologic compositions commonly used for the treatment of BPH:

a) alpha-antagonists (also termed "alpha-adrenergic antagonist"), which act via adrenergic pathways and can be effective in relieving symptoms of BPH, but do not alter prostate size. The alpha-antagonist can be selective for either alpha 1- or alpha 2-adrenergic receptors, or it can be non-selective, exhibiting antagonist activity at both alpha 1- and at alpha 2. The three most popular synthetic pharmacologic alpha-1-adrenergic antagonists which have been approved by the FDA for the treatment of the symptoms of BPH are terazosin (Hytrin®), doxazosin (Cardura®), and tamsulosin (Flomax®).

b) 5-alpha-reductase inhibitors: inhibiting the enzyme 5-alpha-reductase, in particular type II which is present in the prostate and converts testosterone into dihydrotestosterone (DHT). 5-alpha reductase inhibitors act via hormonal mechanisms and have been shown to reduce prostate volume. An exemplary competitive and specific inhibitor of Type II 5-alpha-reductase is Finasteride (Proscar®). The usefulness of finasteride has been somewhat limited due to a multitude of undesirable side effects including impotence, decreased libido, and ejaculatory disorders. Furthermore, finasteride causes a decrease in serum prostate specific antigen (PSA) levels by approximately 50% in patients with BPH, even in the presence of prostate cancer. This lowering of serum PSA levels may obscure its utility as a tumor marker for prostate cancer.

Evidence now suggests that patients with moderate to severe symptoms and smaller prostates (estimated volume less than or equal to 30 cc or serum PSA less than or equal to 1.4 ng/ml) are more likely to benefit from monotherapy with alpha-1-adrenergic antagonists, while those with comparable symptoms and larger prostates (estimated volume >30 cc or serum PSA >1.4 ng/ml) may derive more durable results from combination therapy of an alpha-1-adrenergic antagonist (for example terazosin), alleviating the dynamic component of obstruction, and a 5-alpha reductase inhibitor (for example finasteride), which reduces prostate size thereby addressing the mechanical component of obstruction.

Phytotherapeutic agents (also known as plant extracts) have been suggested as a natural alternative for the treatment of symptoms associated with BPH. Some of the more common plant extracts prescribed for BPH are obtained from: *Serenoa repens* (Saw Palmetto Berry), *Pygeum africanum* (Plum Bark) and *Cucurbita pepo* (Pumpkin Seed). However, recently their efficacy has been questioned (see for example, "Saw Palmetto for Benign Prostatic Hyperplasia", S. Bent et al., in The New England Journal of Medicine, Vol. 354 (6): 557-566 (2006)).

*Opuntia ficus-indica* (OFI), otherwise known as nopal or prickly pear, belongs to the genus *Opuntia*, the most common and widespread genus among the cactus (Cactaceae) family. It has been widely used as a folk remedy for treating burn, edema, indigestion and bronchial asthma. As all cactus species, the OFI plant can be morphologically divided into root, stems (cladodes), fruit and flower.

Most of the research on medicinal uses of this plant has been conducted on the cladodes and on the fruits and the medicinal uses of the flowers of the OFI have hardly been investigated:

Japanese patent publication No. 10059995 (to Shikei et al.) has isolated specific flavonoid derivatives by a methanol extraction of OFI flowers followed by a complex series of chromatographic purification steps and has further demonstrated that the specific bioflavonoid isorhamnethin 3-o-robinibioside, which is obtained by this process, may serve as an inhibitor of 5-alpha-reductase. Not only is this process complicated, expensive and prohibitive from an industrial point of view, Shikei has also failed to show any extract exhibiting alpha blocker activity and has further failed to show a method of inhibiting alpha blocker activity and/or treating humans suffering from BPH by using any of these extracts.

Another in vitro study (Jonas A et al., Urol. Res. 1998; 26: 265-270) suggested that the dichloromethane, ethanol or methanol extracts of the OFI flower, obtained under a prolonged high-temperature reflux, might be helpful to treat prostate enlargement by inhibiting the 5-alpha-reductase activity. However, Jonas et al. have failed to show any extract exhibiting alpha blocker activity under these conditions, have failed to provide a water-soluble effective extract, devoid of organic and/or waxy impurities, and have further failed to show a method of inhibiting alpha blocker activity and/or treating humans suffering from BPH by using any of these extracts.

Thus, there has yet been no teaching of any natural products claiming to have an alpha blocker activity. In particular, there has yet been no teaching of any alpha blocker activity of the flower of OFI or any of its components. Furthermore, there has been no therapeutically active OH flower extract which is substantially water-soluble, and can have improved bioavailability in the body.

Accordingly, there is a long felt need for a natural therapeutic, preferably water-soluble, composition and method for inhibiting alpha-1-adrenergic receptor, and further for a natural therapeutic composition for inhibiting both alpha-1-adrenergic receptor and 5-alpha reductase activity, which do not have the adverse effects of the prior art compositions and methods and are suitable and proven in clinical studies, to be used effectively for the treatment or alleviating symptoms by administering a compound having characteristics of inhibiting alpha-1-adrenergic to humans suffering from BPH.

The present inventors have now successfully isolated and prepared a water-soluble alcoholic extract of the OH flower, which has a proven alpha-1-adrenergic receptor inhibition and was even successful in treating, preventing or alleviating urinary tract disorders, such as BPH, in clinical trials in vivo in human subjects. This extract was prepared to be substantially free of any non-water soluble residues and is therefore especially suitable as a therapeutic agent, having an improved bioavailability.

Thus, according to one aspect of the invention, there is provided a water-soluble alcoholic extract of *Opuntia ficus-indica* flower (NABIA extract), a component thereof (NABIA fraction) or any mixture of components thereof, which is substantially free of non water-soluble residues, and exhibits an effective alpha-1-adrenergic receptor blocking activity.

As used herein, the term "water soluble" refers to a solubility in water at a level of at least about 10% by weight, and preferably at least about 20% by weight, although typically, aqueous plant extracts may have a much higher solubility in water.

Furthermore, the term "water soluble" is meant to refer to both solid and liquid extracts, and therefore also encompasses the term "water miscible" which generally refers to liquids miscible in water and means a liquid that can be added to water without resulting in the formation of a separate phase.

The term "extract", used interchangeably with the terms "plant extract", "herbal extract" or "botanical extract", as used herein refers to a substance or composition obtained from a plant or plant part source, regardless of whether the substance or composition is found external to the plant (i.e., an exudate), is found within the plant or plant part but external to the cells thereof, or is found within the cells of the plant. Chemical and/or physical action, as would be understood in the art, may be required to obtain the substance or composition from the plant or plant part. The extract of the present invention is obtained from OH flowers.

This extract exhibited an effective alpha-1-adrenergic receptor blocking activity, as demonstrated in Examples 5 (in vitro experiments) and 7 (in vivo experiments on human subjects), this being the first time that such an activity was found in a plant extract, and further this being the first time that a plant extract was effectively used to inhibit alpha-1-receptor activity and to effectively treat humans suffering from BPH, a common urinary tract disorder.

The phrase "alpha-1-adrenergic receptor blocking activity" or "alpha-1-blocking" or "alpha-1 inhibition" includes any ability to effectively act on or bind to alpha-1-adrenergic receptors and provide a therapeutic effect.

Thus, the phrase "alpha-1-adrenergic agonists" or "alpha-1-blockers" includes any chemical entities within the extract, for example extract fractions, specific compounds, ions, complexes and the like, which are effective to act on or bind to alpha-1-adrenergic receptors and provide a therapeutic effect.

Alpha-1-inhibition can be measured by any number of methods known in the art, some of which are described in the methods section hereinbelow. One way to characterize the alpha-blocker activity is through the half maximal inhibitory concentration ($IC_{50}$) values, which is a measure of concentration used in pharmacological research, representing the concentration of an inhibitor that is required for 50% inhibition of its target, in this case alpha-1-adrenergic receptors.

Alternatively, the percent of inhibition is also used as a measure of activity, oftentimes in comparison to synthetic alpha-1 blockers, for example as shown in Tables 3 and 4 below.

It has now been found that the extracts of the present invention can inhibit alpha-1-receptors both non-specifically and specifically.

As used herein the terms "specifically", "specific", "selectively" and "selective" are used interchangeably. For example, Table 2 in Example 5 compares the non-specific alpha-1-inhibition of several compounds. As shown therein, the common natural product used in BPH treatment, saw palmetto, has an alpha-1 $IC_{50}$ of about ~$3*10^{10}$ ng/ml, a value which is 8 orders larger than the common synthetic alpha blocker, terazosin. For all practical purposes, such a high value signifies a non-existent alpha-1-blocker activity. In contrast, the extract of the present invention had an alpha-1 $IC_{50}$ as low as $10^3$ ng/ml, quite comparable with the most effective synthetic alpha-blocker used today.

Thus, according to a preferred embodiment of the present invention, the non-specific alpha-1 inhibition activity of the present extract can be characterized by a half maximal alpha-1-blocker inhibitory concentration ($IC_{50}$) which is lower than $10^7$ ng/ml. Preferably, the extract is characterized by an $IC_{50}$ which is lower or equal to $10^6$ ng/ml, more preferably by an alpha-1 $IC_{50}$ which is lower than $10^5$ ng/ml, and even lower than $10^4$ ng/ml.

As shown in Table 4 in Example 5 below, it has been surprisingly found by the present inventors that the NABIA extract also successfully blocked specific alpha-1-receptors. For example, at a 50 µg/ml concentration, the NABIA extract showed an alpha-1A and alpha-1B inhibition of 99%, as compared to a WB 4101 control, and to a prazosin control, respectively, whereas at the same concentration the extract showed an alpha-1C inhibition of 103% as compared to a prazosin control. Similar results were obtained in a 300 µg/ml concentration.

Therefore, according to a preferred embodiment of the present invention, there is provided a NABIA extract which exhibits a selective alpha-1 blocking activity for any of alpha-1A ($\alpha_{1A}$), alpha-1B ($\alpha_{1B}$) or alpha-1D ($\alpha_{1D}$) adrenergic receptor.

It was now been further unexpectedly found by the present inventors that the NABIA extract also exhibited a 5-alpha-reductase inhibition effect, as can be seen in FIG. 3 which shows that fractions D, F and G of the NABIA extract reduced the activity of the 5-alpha-reductase enzyme to about 10% of the original activity. Similar results were obtained for the NABIA extract obtained according to Example 2.

Thus, according to a preferred embodiment of the present invention, the extract of the present invention further exhibits a 5-alpha-reductase inhibition activity, and therefore has both alpha-1-blocking activity and 5-alpha-reductase inhibition, thereby forming the first natural extract to provide both these effects in one completely-natural product.

A variety of mildly polar fluids, such as alcohols, can be used to extract efficacious materials from plants such as OFI. Thus, the extract of the present invention is an alcoholic extract, obtained through the extraction of the OFI flower from common alcohols, such as methanol, ethanol, and isopropanol and any aqueous solutions thereof.

While some alcoholic extracts of OFI flowers have been prepared in the art, for example in Jonas (1998, supra) and in Japanese patent publication No. 10059995, the present inventors have now devised a special process of obtaining the extract, such that it is substantially free of any non-water soluble residues.

As used herein, the phrase "substantially free of any non-water soluble residues" refers to levels that are low enough to prevent any visual deposition of these non-water soluble residues.

In fact, as is detailed in the examples section below, the process devised by the present inventors resulted in a clear, dark liquid or semi-liquid extract from which any non-water soluble residues had already been removed and the addition of water to this extract did not adversely affect its clarity. When dried, this extract was easily re-dissolved in water to obtain the same clear solution. It should be noted that the clarity of the water-soluble extract was maintained even after prolonged shelf life, and was manifested also in any individual fractions of the extract.

Thus, according to a preferred embodiment of the present invention, a water-soluble extract which is substantially free of any non-water soluble residues will appear as a clear solution when placed in water. For example, in order to test whether a specific OFI alcoholic extract is water soluble and substantially free of any non-water soluble residues, one can take add 50 ml water to a 50 gram sample of the extract, mix them for at least 2 hours at room temperature and observe the obtained solution upon 24 hours from beginning of mixing. A clear solution obtained under such conditions can invalidate the existence of non-water soluble residues therein.

The term "clear" as used herein describes a solution that does not contain any visible solids or suspensions, and is not necessarily a transparent one.

Examples of non-water soluble residues which are in an OFI extract may include waxes, oily compounds and other organic substances.

In order to obtain such an extract, several measures were now taken by the present inventors:

First, the initial alcoholic extraction stage was performed on dried and crushed OFI flowers at a relatively low temperature, preferably at about room temperature in order to prevent the dissolution in alcohol of the less alcoholic-soluble substances, such as waxes and oils, and obtain a primary extract. Preferably, the alcoholic solvent was selected from methanol, ethanol or propanol. As an optional feature of the process, the alcoholic extract used to obtain this primary extract preferably contains water, either by using an aqueous alcoholic solvent (as in Example 2) or by using a 100% alcoholic solvent (as in Example 1).

According to one preferred embodiment of the present invention, most or all of the alcoholic solvent is completely evaporated from the primary extract to obtain a secondary extract which is already somewhat water-soluble. To this extract water may be added as described further bellow.

The inventors have further found that if this secondary extract is kept under conditions enhancing deposition of any residual non-water soluble substances, for example under cooling to about 4-10° C., or at room temperature, for at least several hours, it is possible to deposit any residues remaining in said secondary extract, and then separate them to obtain a water-soluble alcoholic extract which is substantially free of any non water-soluble residues, and which exhibits an alpha-1-blocker activity, as described hereinabove.

Thus, according to another aspect of the invention, there is provided a process for preparing the clear, water-soluble alcoholic extract of *Opuntia ficus-indica* flower described herein, whereas this process comprises:

a) obtaining naturally dry *Opuntia ficus-indica* flowers;
b) crushing and grinding the OFI flowers to obtain an OFI flower powder;
c) extracting the powder in an alcoholic solvent, at room temperature to obtain a primary extract solution containing a primary extract and an exhausted flower;
d) separating the exhausted flower from the primary extract;
e) evaporating any alcoholic solvent from the primary extract solution to obtain a secondary extract;
f) depositing any non water-soluble residues from the secondary extract; and
g) separating the non water-soluble residues from the secondary extract to obtain a clear water-soluble alcoholic extract of the *Opuntia ficus-indica* flower which is substantially free of any non water-soluble residues. This extract was termed NABIA extract.

According to another preferred embodiment of the present invention, in order to enhance the deposition described herein, water is preferably added to the secondary extract prior to the deposition, followed by heating the obtained secondary extract including the added water, to above 50° C., and even above 80° C., to ensure a complete dissolution of the non water-soluble residues prior to their deposition.

It should be clarified that the addition of water described herein is done to increase the workability of the extract, which otherwise has a very high viscosity, and to decrease solvent content at the final stages to enable easier and more complete separation of any organic deposited materials.

Thus, according to another aspect of the invention there is provided an alternative process for preparing the clear, water-soluble alcoholic extract of *Opuntia ficus-indica* flower of any of claims 1-4 (NABIA extract), this process comprising:

a) obtaining naturally dry *Opuntia ficus-indica* (OFI) flowers;
b) crushing and grinding said OFI flowers to obtain an OFI flower powder;
c) extracting said powder in an alcoholic solvent, at room temperature to obtain a primary extract solution containing a primary extract and an exhausted flower;
d) separating said exhausted flower from said primary extract;
e) evaporating said alcoholic solvent from said primary extract solution to obtain a secondary extract;
f) adding water to said secondary extract;
g) heating to above 80° C.;
h) depositing any non water-soluble residues from said secondary extract, wherein said depositing is conducted under overnight cooling; and
i) separating said non water-soluble residues from said secondary extract to obtain a clear water-soluble alcoholic extract of the *Opuntia ficus-indica* flower, which is substantially free of any non water-soluble residues (NABIA extract).

As have been preferentially found by the inventors, the depositing of the non water-soluble residues from the secondary extract is conducted either at room temperature, or under cooling. According to a preferred embodiment of the present invention, this step is conducted overnight.

Where stated, the term "room temperature" refers to a temperature from 15 to 30° C. and the term "overnight" refers to a time from 8 to 18 hours. As any person skilled in the art would appreciate, longer deposition times are possible. The term "cooling" as used herein refers to a temperature which is lower than room temperature and preferably ranges from about 4° C. to about 15° C., more preferably from about 4° C. to about 10° C.

It should be noted that the relatively low yield of the extract in the suggested process (between 5% and 20% yield relative to the dried flower weight) demonstrates the ability of the inventors to successfully isolate the effective ingredients in the OFI flower, thereby obtaining an extract which exhibits a unique alpha-1-blocker activity, which has not yet been found in a natural product.

Furthermore, the inventors have shown that the OFI extract obtained according to the process disclosed herein, may be further purified and separated into yet additional components. Exemplary purification methods may include chromatographic separation, selective precipitation or selective solvent extraction.

It has been found that extract fractions obtained through the additional purification can be further classified according to their biological activity, and therefore selection of specific active fractions of the extract is made possible.

Thus, according to yet another preferred embodiment of the present invention, the term "extract" of the present invention also includes separate components of this extract, or a combination of two or more of these components, as long as these components also exhibit an alpha-1-blocker activity as described hereinabove.

As has been shown in the Examples section which follows, it was found that chromatographically separated fractions of an OFI flower produced only three fractions that showed an alpha-1-blocking activity. These fractions were termed NABIA fraction D, NABIA fraction F, and NABIA fraction G, and were ultimately combined into one NABIA extract exhibiting the same alpha-1-blocker activity and also appearing as clear water-soluble extracts being substantially free of any non-water-soluble extracts, as described hereinabove.

Thus, according to a preferred embodiment of the present invention, there are provided the specific NABIA fractions D, F and G, and any combinations thereof.

Although it appears from Table 1 that these fractions contain a series of polyphenols and flavonoids (some of which were identified), it is difficult to tell which chemical compounds within the extract, or within the extract fractions, are responsible for the alpha-1-blocker activity. Without being bound to any specific theory, it was found that NABIA typically comprises from about 2% to about 90% of polyphenols and flavonoids.

It was further shown by the inventors that by conducting the initial extraction with an aqueous alcoholic solvent (as in Example 2), it was possible to easily obtain a water-soluble alcoholic extract having the same alpha-1-blocker activity, and the same chemical fingerprinting of the NABIA obtained by the first process (Example 1), without conducting any additional purifications, such as the chromatographic separation, which is obviously preferred from an economical and industrial point of view.

The NABIA extract obtained by the processes described herein is initially obtained as a liquid form, which is termed a liquid NABIA extract.

However, an additional drying step may be conducted, by any conventional drying methods, to obtain the NABIA extract in a solid form, which is termed a dry NABIA extract.

It has been found that both liquid and dry NABIA extracts proved to be very stable, being stable for at least 3 months both at room temperature and at 50° C., in terms of alpha-1-blocker activity as well as in terms of water retention. However, if an even longer shelf life is required, it may be necessary to add a preservative to this extract.

The extracts described herein may also form part of formulation, whereby a carrier is added to the extract described herein.

For example, the formulation may be a phytotherapeutical formulation, a nutritional formulation, a nutraceutical formulation, or a pharmaceutical formulation, according to the required use thereof.

The term "nutritional formulation" as disclosed herein refers to formulations having at least one physiological function when administered to a mammal by conventional routes of administration.

The term "nutraceutical" refers to any compounds or chemicals that can provide dietary or health benefits when consumed by humans or animals, encompassing usefulness in both the nutritional and pharmaceutical field of application. Thus, nutraceutical formulations can be useful as a complete human food or animal feed (diet or dietary foods), as supplement to human food or animal feed, and as pharmaceutical formulations for enteral or parenteral application which may be solid formulations, or liquid formulations.

The term "dietary food" is used interchangeably with the terms "dietary food", "dietary supplement", "food supplement" and "dietary ingredient", referring to ingestible substances which are capable of eliciting a desired health effect, such as weight loss, controlling weight gain, and/or reducing body mass index to acceptably healthy levels. More specifically, as used herein, this term refers to ingestible substances which act to alleviate, prevent or treat urinary tract disorders.

Furthermore, it should be noted that the terms "nutritional supplements", "food supplements", "dietary supplements" and the like generally encompass any compositions which do not belong to the conventional definition of pharmaceutical formulations, as those are known in the art.

Hence, the carrier may be a pharmaceutically acceptable carrier, or a carrier acceptable in food applications or a combination of both, such as a nutraceutical carrier.

Thus, according to an additional aspect of the present invention, there is provided a formulation comprising the NABIA extract described herein, and a carrier.

As used herein, the term "carrier" denotes a solid or liquid filler, diluent, or encapsulating substance. Some examples of the substances that can act as carriers are sugars such as lactose, glucose, and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and of the broma; polyols such as propylene glycol, glycerin, sorbitol, mannitol, and polyethylene glycol; agar, alginic acid; pyrogen-free water; isotonic saline; ethyl alcohol and phosphate buffer solutions, as well as other non-toxic compatible substances used in preparation of formulations. Preferably, the carrier may be either a liquid carrier, such as water, alcohols, saline, oil and juice, or it may be a solid carrier, such as a carrier selected from the group comprising of maltodextrin, dextrins, silicon dioxide, starches, gums and hydrocolloids. Occasionally, a combination of carrier may be used, for example using maltodextrin or gum arabic as a solid carrier, together with a vegetable oil as a liquid carrier.

By choosing the suitable carrier(s), the formulation may be designed in any required dosage form. Exemplary dosage form include tablets, pills, dispersions, sachet, elixir, suspensions, emulsions, solutions, syrups aerosols, soft or hard gelatin capsules, injection solutions or suspensions, ointments, creams or lotions.

In order to obtain these diverse dosage forms, some additional additives may be required. For example, at least one pharmaceutically acceptable compound selected from the group comprising of a disintegrating agent, a moistening agent, a sweetening agent, a preserving agent and/or a flavoring agent.

It has been shown by the present inventors that the formulations described herein are also highly stable. For example, it was shown that gelatin capsules containing NABIA extract according to a preferred embodiment of the present invention, was stable for at least 3 months both at room temperature and at 50° C.

Since the extracts and formulations described herein effectively inhibited alpha-1-adrenergic receptor activity, and even inhibited 5-alpha reductase enzymatic activity, it is obvious that these extracts and formulations are highly suitable for the treatment and prevention of urinary tract disorders (UTD).

Thus, according to another aspect of the invention, there is provided the formulations or extracts described herein, being packaged in a packaging material and identified in print, in or on said packaging material, for use in the treatment of a urinary tract disorder (UTD). The UTD is selected from the group consisting of lower urinary tract syndrome (LUTS), and benign prostatic hyperplasia (BPH).

While the methods, extracts and formulations of the present invention are primarily directed, but not limited to therapeutic activity related to urinary tract disorders, particularly BPH, they may be effective in therapeutic activities of other disorders which involve activity of enzyme 5-alpha-reductase and/or the alpha-1-adrenergic receptor. The therapeutic methods and compositions of the present invention have been found to be effective in alleviating disorders which involve activity of enzyme 5-alpha-reductase and/or the alpha-1-adrenergic receptor.

Throughout the description the term "therapeutic" also includes preventive activity.

The term "alleviating" is meant to include reducing, preventing, and reversing the symptoms of BPH, or the symptoms of lower urinary tract symptoms (LUTS), such as: increased frequency of urination, nocturia, a weak urine stream, hesitancy or delay in starting the urine flow and incomplete bladder emptying. Additional symptoms that may be alleviated include those associated with chronic consequences of BPH, such as: hypertrophy of bladder smooth muscle, a decompensated bladder, an increased incidence of urinary tract infection, urinary stone formation and renal failure.

This term encompasses those situations wherein these symptoms are completely avoided as well as partially or completely eliminated.

Thus, there are provided the formulations or extracts described herein, being packaged in a packaging material and identified in print, in or on said packaging material, for use in inhibiting alpha-1-adrenergic receptor activity. This inhibition can be non-selective or be selective for any of alpha-1A ($\alpha_{1A}$), alpha-1B ($\alpha_{1B}$) or alpha-1D ($\alpha_{1D}$) adrenergic receptor.

Yet further, there are provided the formulations or extracts described herein, being packaged in a packaging material and identified in print, in or on said packaging material, for use in inhibiting 5-alpha-reductase enzymatic activity.

Naturally, the formulations or extracts described herein may be packaged and identified for several simultaneous uses, as described hereinabove.

As described in the Examples section below, it was now found in clinical trials that the NABIA extracts of the present invention were used to prepare therapeutical formulations that successfully treated human patients suffering from BPH: in 75% of the patients a clear improvement in symptoms was achieved by using a NABIA treatment regime.

Thus, in another aspect of the invention, there is provided a use of any of the extracts described herein, in the manufacture of a medicament for the alleviation of symptoms and/or treating UTD.

Consequently, according to yet another aspect of the invention, there is provided a method of alleviating, treating or preventing a UTD, the method comprising administering to a subject in need thereof a therapeutically effective amount of the NABIA extract or formulation described herein. Furthermore, there is provided a method for inhibiting alpha-1-adrenergic receptor activity, both specific and non-specific, and/or 5-alpha-reductase enzymatic activity, the method comprising administering to a subject in need thereof a therapeutically effective amount of the NABIA extract or formulation described herein.

The term "therapeutically effective amount" shall mean that amount of or extract that will elicit the biological or medical response of a tissue, system, animal or human that is being sought. In the present case, a therapeutically effective amount of a formulation or extract is such an amount that will induce inhibition of alpha-1-adrenergic receptor activity and/or inhibition of 5-alpha-reductase enzymatic activity.

The therapeutically effective amount may be evaluated and described in terms of the UTD response to the treatment, for example as using common indexes, such as the International Prostate Symptom Score (IPSS), peak urinary flow rate ($Q_{max}$), average flow rate (Qavg) and flow time/void time.

The dosage form, daily dosage administered and the length of treatment are determined by the attending clinicians taking into consideration the prostate volume and symptom severity of the disease, the patient's general condition and age, the potency of each component and other factors. It is generally believed that therapeutically effective amounts of the extracts and formulations of the present invention are chosen, such that for a human subject, weighing between 70-100 kilograms, the daily dose ranges from about 3.0 mg extract/day to about 1000 mg extract/day. Preferably, the daily dose ranges from about 100 mg extract/day to about 500 mg extract/day, more preferably from about 200 mg extract/day to about 500 mg extract/day, more preferably from about 200 mg extract/day to about 300 mg extract/day.

The use of therapeutically effective amounts of the natural 5-alpha-reductase inhibitor and the natural alpha-1-blocker in accordance with this invention effectively treats the adverse symptoms of BPH including nocturia, hesitancy, decreased urinary flow, and the like. Furthermore, the use of the therapeutically effective amounts of the NABIA extract, as described hereinabove, achieves a dual effect, wherein the alpha-1-adrenergic inhibition properties of the extract alleviate symptoms of BPH, and the 5-alpha-reductase inhibition properties of the extract reduce the volume of the patient's prostate caused by the BPH.

Depending on the specific dosage form used, the extract or formulation described herein can be administered in any number of ways; most preferably, it is administered orally or parenterally, for example by a percutaneous, subcutaneous, intravenous or intramuscular administration.

Preferably, the compositions provided by the present invention are used as an orally-administrable composition. The term "orally-administrable composition" as used herein includes both pharmaceutical and herbicidal compositions, as well as food supplements within its scope. However, other forms of administration are also possible, as disclosed hereinunder.

In the practice of the methods of the invention, the composition and dosage forms may be administered orally in any of the usual solid forms such as pills, tablets, capsules or powders, including sustained release preparations.

The term unit dosage form as used in this specification and in the claims refer to physically discrete units to be administered in single or multiple dosage to humans, each unit containing a predetermined quantity of active material (NABIA), i.e., NABIA or NABIA in combination with protein, carbohydrate, and fatty acids, and/or NABIA in combination with other botanical extracts like saw palmetto, any of the above in association with one or more carriers. The quantity of active material is that calculated to produce the desired therapeutic effect upon administration of one or more of such units. Of course, it is understood that the exact treatment level will depend upon the case history of the human subject to be treated. The precise administering level can be determined by one of ordinary skill in the art without undue experimentation, taking into consideration such factors as age, size, severity of condition, and anticipated duration of administration on compounds, among other factors known to those of ordinary skill.

Unit daily dosages of net NABIA weight can range from about 1.0 mg/kg to about 100 mg/kg (the unit designated "mg/kg" as used herein refers to mg of NABIA and/or NABIA in combination with protein, carbohydrate, and fatty acids and/or NABIA in combination with other botanical extracts like Saw Palmetto, per kilogram of body weight), preferably from about 1 mg/kg to about 30 mg/kg, most preferably about 2-20 mg/kg. The doses can be administered in any convenient dosing schedule to achieve the stated beneficial effects. For example, the doses can be taken 1, 2, 3, 4, 5 or more times daily. Preferably 1-3 doses are taken daily. Most preferably, the doses are taken at meal times. The dosages may be taken orally in any suitable unit dosage form such as pills, tablets, and capsules. Preferred are capsules made from gelatin.

According to a preferred embodiment of the present invention, the preferred dosage form is a capsule comprising from 3 mg extract to 1000 mg extract, preferably comprising from 100 mg extract to 1000 mg extract per day per person.

Other preparations that can be used orally include push-fit capsules made of gelatin, as well as soft, sealed capsules made of gelatin and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Powder dosage forms are prepared by comminuting the compositions of the present invention to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added improve the availability of the medicament when the capsule is ingested.

Tablets are made by preparing a powder mixture, granulating or slugging, adding a lubricant and disintegrant and pressing into tablets. A powder mixture is prepared by mixing the compositions of the present invention, suitable comminuted, with a diluent or base such as starch, sucrose, kaolin, dicalcium phosphate, zinc and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The active ingredients can also be combined with free flowing inert carriers and compressed into tablets directly without going through the granulating or slugging steps. A protective coating consisting of a sealing coat of shellac, a coating of sugar or polymeric material and a polish coating of wax can be provided. Dye stuffs or pigments may be added to the tablets, for example, for identification or in order to characterize combinations of active doses. In tablet form the carrier comprises from about 0.1% to 99.9% by weight of the total composition.

Additional objects, advantages, and novel features of the present invention will become apparent to one ordinarily skilled in the art upon examination of the following examples, which are not intended to be limiting. Additionally, each of the various embodiments and aspects of the present invention as delineated herein and as claimed in the claims section below finds experimental support in the following examples.

EXAMPLES

Figure 1:
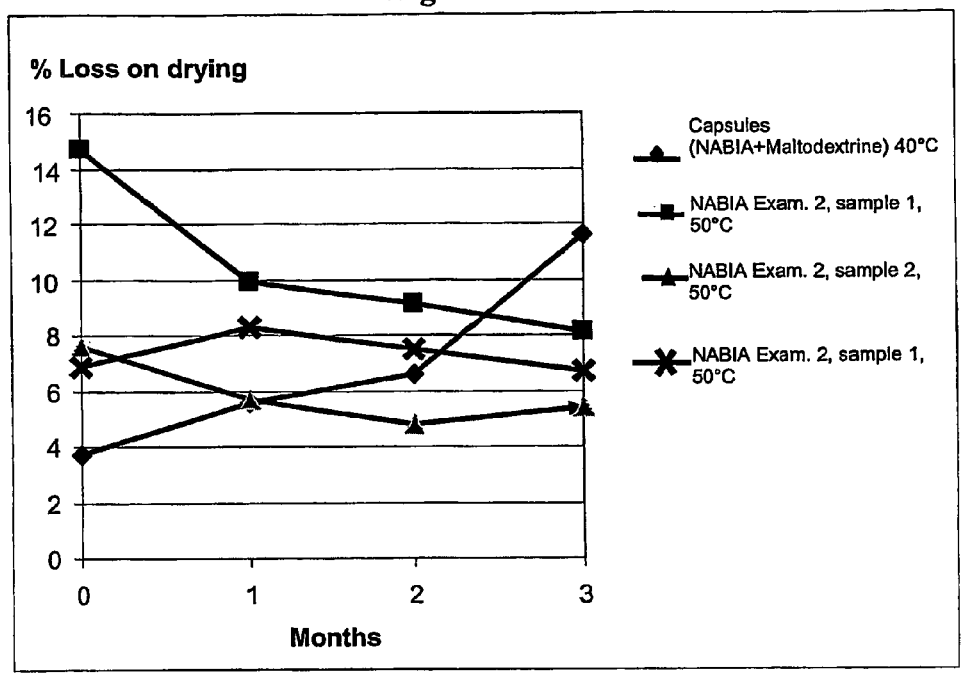
FIG. 1 is a graph showing the loss on drying (%) of NABIA maltotextrine capsules and NABIA extracts over a period of three months, at 40° C. and at 50° C.

Reference is now made to the following examples, which together with the above descriptions, illustrate the invention in a non limiting fashion.

Product Preparation

Materials and Analytical Methods:

All reagents, solvents and starting materials were purchased from known vendors such as Sigma, Fluka, Aldrich and Merck, unless otherwise indicated.

Dry flowers of *Opuntia ficus-indica* (L.) Miller (OFI) were obtained from fields located in Southern Israel, having a specified plant variant termed Ofer. Plants were neither hybrid nor transgenic. The flowers were collected several days after having naturally dried in the field, and were visually inspected by a professional botanist for fungi and other potential diseases.

Dry flowers were manually cropped and grinded using a conventional hammer mill.

Chromatographic separation was performed using 100 cm silica gel (70-230 mesh, 60 Å particles, Aldrich catalogue number 28,862-4) columns having a diameter of 4.5 cm. A preliminary washing of the columns was performed using Hexane. Separation was conducted at atmospheric pressure using a flow rate of 1.7-2.0 ml per minute. The different fractions were characterized using fingerprint analysis, as follows.

The total flavonoid content (%) was measured using UV-VIS spectrophotometer HP 8453, at a wavelength of 410 nm.

The total phenols content was measured using UV-VIS according to the Folin-Denis (vs. Ciocalteu) method UV-VIS spectrophotometer HP8453, at a wavelength of 760 nm.

GC-MS was used to determine the volatiles content, using a Hewlett Packard 5890/5970 GC/MS system HPLC was used to determine the fraction fingerprint, using an HPLC system manufactured by Merck-Hitachi Intelligent Pump (model L6200A), equipped with UV/VIS detector L-4250 and HP-ChemStation software.

HPLC column used was a Merck 1.50359 RP-18(e), 5 μm, obtained from Purospher Star, LiChroCART 250-4.

Water loss was measured by AOAC Official Method 935.29.

Example 1

Preparation of Extracts of OFI Flowers—Route A

Naturally dry raw Opuntia ficus-indica (OFI) flowers (100 grams) were cropped and grinded in a hammer mill to obtain a coarse powder. This powder was then extracted by Methanol 100% step-by-step, using 1:10, 1:10, 1:5, 1:5 w/v ratio, such that the total volume of solvent used was 3 liters. The total time of extraction was 9 hours at room temperature. After filtering the exhausted plant, all extracts were combined into one solution and were distilled at up to 40° C. under vacuum (20-30 mbar) to obtain a dry residue (15-17 grams, 15-17% yield) which was re-dissolved in methanol (50-70 ml), and placed overnight at 4° C. Any remaining waxy and/or fatty residues were then removed from the residual extract by filtration through a Whatman paper filter #1 with the addition of filter aid materials like Celite.

In order to prepare the treated extract for chromatographic separation, the filtrate was mixed with 60 grams of Silica gel and dried under vacuum until a constant weight was obtained. Finally, a chromatographic separation was conducted using the same Silica gel (ratio dried extract-Silica gel 1:10 w/w), and the following eluents:
   a) n-Hexane 100%, total volume—1000 ml,
   b) n-Hexane-Chloroform 5:1 (v/v), total volume—2000 ml
   c) n-Hexane-Chloroform 1:1 (v/v), total volume—2000 ml
   d) n-Hexane-Chloroform 1:5 (v/v), total volume—2000 ml
   e) Chloroform 100%, total volume—2000 ml
   f) Chloroform-Methanol 20:1 (v/v), total volume—2000 ml
   g) Chloroform-Methanol 10:1 (v/v), total volume—2000 ml
   h) Chloroform-Methanol 5:1 (v/v), total volume—2400 ml, 24 fractions of 100 ml of each (numbered 1-24), collecting the last ten fractions of this step).
   i) Chloroform-Methanol 1:1 (v/v), total volume—2000 ml (20 fractions of 100 ml of each (numbered 25-44), collecting the first ten fractions of this step)

During separation all fraction were monitored by TLC. Fractions obtained at stages a)-g) were discarded. Evaporation under vacuum was conducted for the 20 fractions of steps h) and i). These fractions were screened for a desirable biological activity, and the 5 first fractions of the step i) have demonstrated it. According to their chemical content and biological activity these fractions were combined giving fraction termed NABIA D (yield 3.9%, calculated on extract before chromatographic separation), E (12.3%) and G (14.6%). The chemical composition of the biologically active fractions is presented in Table 1 below:

TABLE 1

| Fraction | Total flavonoids | Total phenols | Identified flavonoids |
|---|---|---|---|
| NABIA-D | 51.36% | 7.57% | Narcissin 1.8% |
|  |  |  | Isoquercitrin 3.3% |
|  |  |  | Astragalin 1.9% |
|  |  |  | Rutin 6.2% |
| NABIA-E | 33.96% | 6.34% | Luteolin, 1.4% |
|  |  |  | Taxifolin, 2.1% |
|  |  |  | 7-Hydroxyflavone, 1.9% |
| NABIA-G | 12.88% | 4.27% | Myricetin, 1.1% |
|  |  |  | Isoliquiritigenin, 1.6% |
|  |  |  | 7-hydroxyflavanone, 1.8% |
|  |  |  | Penduletin 0.9% |

Fractions D, E and G were re-combined to achieve their natural ratio thereby maintaining a clear, black water-soluble liquid extract that was termed "NABIA".

Example 2

Preparation of Extracts of OH Flowers—Route B

Naturally dry raw OFI flowers (1000 grams) were cropped and grounded to obtain dry OFI flowers particles smaller than approximately 2 mm, followed by extraction from ethanol (80%, 6 volumes, 6 liters) during 3-5 hours at room temperature. After filtering the exhausted plant, the ethanolic extract was evaporated at lower than 80° C., reducing the solvent volume by about 50-fold to obtain a water-soluble thick-flowing dark liquid residue (300 grams of a 30-40% dry weight aqueous solution. To induce separation of any waxy or organic impurities therein, water (300 ml) were added and the extract was then cooled overnight at between 10° C.-25° C., optionally heating the extract to above 80° C. for about 4 hours before cooling it. Any deposited waxy and/or fatty impurities were removed by filtration and/or by passing through celite, to obtain a clear, black water-soluble liquid extract that has the same chemical fingerprinting of the "NABIA" obtained according to Example 1, and is therefore also termed NABIA. The NABIA extract may be used as is, may be dried and used a free-flowing powder, and may be further processed to form a part of capsules, tablets and other forms of administration, Example 3

Preparation of OFI Capsules

Water (300 grams) was added to the clear, black water-soluble liquid OFI extract obtained according to Example 1 or 2 (100 grams), and the obtained aqueous solution was mixed with maltodextrin (30 grams) and/or gum arabicum (30 grams) for 20 minutes at 70° C., and was then spray-dried to a free-flowing powder (60 grams, 93% yield).

The powder (60 grams) was filled into hard shell gelatin capsules. Optionally, olive oil or another vegetable oil, such as saw palmetto oil (20-50 grams) was added to the powder before encapsulation.

The Herbal Extract Ratio (HER) of the final product ranged from 1:5 to 1:20 by weight extract per original dry flower weight, and therefore signifies the efficiency of the extraction process. The batch-to-batch consistency was maintained by controlled manufacturing procedure, in process control procedure and by standard analytical methods and Bioassays.

Figure 2:
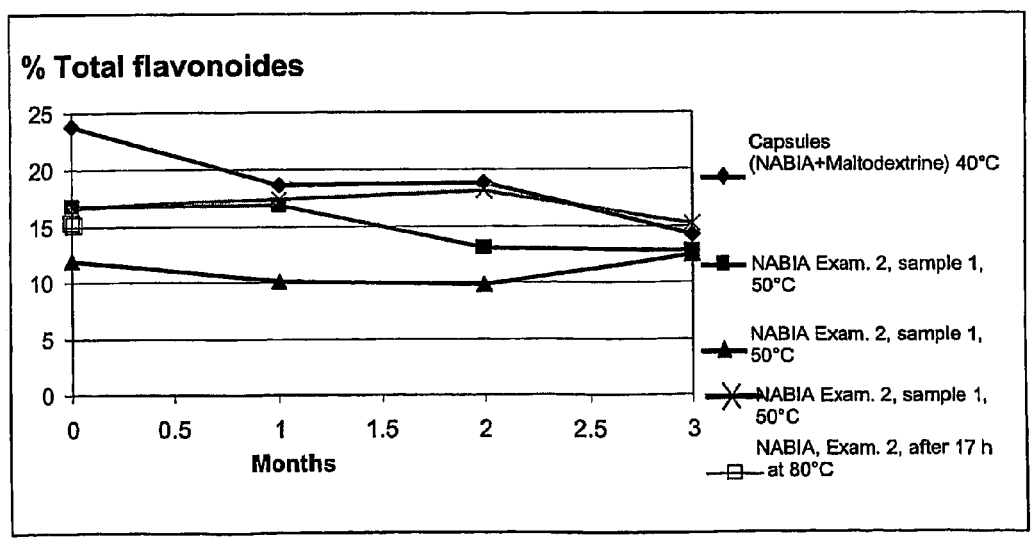
FIG. 2 is a graph showing the total flavonoid content (%) of NABIA maltotextrine capsules and NABIA batches over a period of three months, at 40° C. and 50° C.

The capsules proved to be stable in terms of biological activity, water retention and flavonoids content, over a period of at least 3 months, as can be seen in FIGS. 1 and 2.

FIG. 1 is a graph showing the loss on drying (%) of NABIA maltotextrine capsules and NABIA extracts over a period of three months, at 40° C. and at 50° C.

FIG. 2 is a graph showing the total flavonoid content (%) of NABIA maltotextrine capsules and NABIA batches over a period of three months, at 40° C. and 50° C.

Activity Assays

Materials and Experimental Methods:

Nicotinamide adenine dinucleotide phosphate (NADPH) was obtained from Calbiochem.

Finasteride-MSD (Pro-Cure™) was obtained from Merck.

Terazosin, Prazosin, WB 4101, Tris-HCl, Sucrose, EDTA were obtained from Sigma.

Testosterone, Tween-80 and Phentolamine were obtained from Fluka.

[1,2,6,7,-3H(N)]testosterone and [$H^3$]prazosin were obtained from Du Pont

Crude enzyme extract containing 5-alpha-reductase was isolated from human hypertrophic prostate tissue obtained by surgery from hospital.

Dubecco's modified Eagle medium, fetal calf serum (10%), L-glutamine (2 mM), gentamycine sulfate and amphoterycin B were obtained from Biological Industries, Israel.

Filter manifold was obtained from Pharmacia.

Fiber-glass filters were obtained from Whatman (GF/C).

Thin Layer Chromatography (TLC) was performed using TLC plates—CM. Silica Gel 60 F254 obtained from Merck.

Liquid scintillation counting was performed using Racbeta 1209.

Homogenization was conducted using an ULTRA-TURRAXT 25 homogenizer.

Animals: Female Wistar rats were obtained from Technion vivarium.

Fibroblast culture preparation for 5-alpha-reductase assays: Fibroblasts were grown in 75-$cm^2$ plastic flasks (Corning N.Y.) in Dubecco's modified Eagle medium, containing 4500 mg/l glucose, and supplemented with fetal calf serum (10%), L-glutamine (2 mM), gentamycine sulfate (50 mg/ml) and amphoterycin B (2.5 mg/ml). The culture was incubated at 37° C. in a 5% $CO_2$ atmosphere until confluent. Fibroblast cultures were sub-cultured by trypsinization and used between the third to eighteen-passage number.

Membrane Preparation for Alpha Adrenoreceptors Blocker Assay

The alpha-1 and alpha-2 antagonist activity can be determined using a number of conventional assays in vitro. Suitable assays include those disclosed in U.S. Pat. No. 5,340,814 which employs rat brain cortex membranes, as follows:

Female Wistar rats (180-200 grams) were decapitated and the brain rapidly removed. The cerebral cortex was homogenized in 10 volumes (w/v) of ice-cold buffer containing tris-HCl (5 mM), sucrose (250 mM) and EDTA (1 mM), at pH 7.5, using a homogenizer. The homogenate was centrifuged for 10 minutes at 1000 g, the pellet was discarded and the supernatant was centrifuged at 50,000 g for 15 minutes at 4° C. The final pellet was resuspended in assay buffer and stored at −70° C. for later use. All membrane-preparation procedures were conducted at 4° C.

Alpha-1-Adrenoreceptors Blocker—Binding Assay:

In order to assess the alpha adrenoreceptor blocker activity, binding of [$H^3$]prazosin was measured, according to Catret M et al. 1998 (Catret M., Anselmi E., Ivorra M. D., Elloriaga M., Tur R., D'Ocon M. P. Alpha-adrenoceptor interaction of tetrandrine and isotetrandrine in the rat: functional and binding assays. J Pharm Pharmacol. November 1998; 50(11):1267-73) in samples of diluted membranes, incubated in Tris-HCl buffer (50 mM, Ph 7.4) containing EDTA (0.5 mM) and [$H^3$]prazosin (4 nM), in the absence or presence of several concentrations of the indicated agents. The incubation volume was 200 μl (150 μg protein/tube). The assay tubes were incubated for 90 minutes at 25° C. and the binding reaction was then terminated by rapid vacuum filtration using filter manifold using fiber-glass filters. The filters were then washed with ice-cold Tris-HCl-EDTA buffer (50 mM), at pH 7.4 with the addition of Tween-80 (0.1%, 20 ml). Radioactivity bound to the filters was determined by liquid-scintillation counting. Non-specific binding was defined as binding in the presence of phentolamine (10 μM). The inhibition was defined in terms of the $IC_{50}$.

5-alpha-reductase screening assay: 5-alpha-reductase activity was assayed by decomposing nicotinamide adenine dinucleotide phosphate (NADPH) in a system which contained liver microsomal fraction (containing 5-alpha-reductase), testosterone and the test compound. NADPH decomposition (proportional to 5-alpha-reductase activity) was measured spectrophotometrically at 340 nm, according to Sun Zu-Yue et al. (1998) (Sun Zu-Yue, Zheng Wei-Jun, Feng Jie, Tu Zeng-Hong "A convenient and rapid method to study enzymatic kinetics of steroid 5-alpha-reductase inhibitors" Indian Journal of Pharmacology 1998; 30: 257-262.) with minor modification, wherein in order to multiply the productivity an ELISA-reader was used as a spectrophotometer. Finasteride was used as positive control in this model. Each extract was assayed at 3 different concentrations, and each test was repeated at least 6 times.

5-alpha-reductase type II assay: 5-alpha-reductase type II activity was assessed by reduction of [1,2,6,7,-3H(N)]testosterone in enzyme mixture, containing NADPH, with and without test substances. Steroids were extracted from the reaction mixture and separated by TLC, according to Brooks JR et at (1981) (Brooks J. R., Baptista E. M., Berman C., Ham E. A., Hichens M., Johnston D. B. R., Arth G. E. "Response of rat ventral prostate to a new and novel newel-5-alpha-reductase inhibitor.", Endocrinology, 109 830-836, 1981). The radioactivity of dihydrotestosterone (DHT) was determined by liquid scintillation counting.

5-alpha-reductase: human foreskin fibroblasts assay: The 5-alpha-reductase activity in cultured fibroblasts was measured according to Evans et al. (1995) (B. A. J. Evans, K. Griffiths and M. S. Morton, "Inhibition of 5-alpha-reductase in genital skin fibroblasts and prostate tissue by dietary lignans and isoflavonoids" Journal of Endocrinology (1995) 147, 295-302). Cells were incubated 5 hours with serum-free medium at pH 7.0 containing [1,2,6,7,-$^3$H(N)testosterone. Following the incubation, aliquots of the incubation medium were extracted twice with ethyl acetate and then analyzed by TLC as described previously (Brooks JR et al (1981), supra). In this bioassay dihydrotestosterone (DHT), the product of the reaction catalyzed by 5-alpha-reductase, was measured and the quantity of DHT obtained in reaction without inhibitor was used as a negative control (100% activity or 0% inhibition). The quantity of DHT obtained in reaction with the various inhibitors was calculated as percentage of the negative control.

Bioassay Activity Results

Example 4

5-Alpha-Reductase Inhibition

The different OFI extracts and fractions were tested for 5-alpha-reductase inhibition activity in a human foreskin fibroblasts model, and showed a wide spectrum of results; ranging from 5-alpha-reductase activators to strong 5-alpha-reductase inhibitors.

The most promising results as inhibitors were obtained for the extract fractions D, F and G and for the NABIA obtained according to Example 2.

Figure 3:
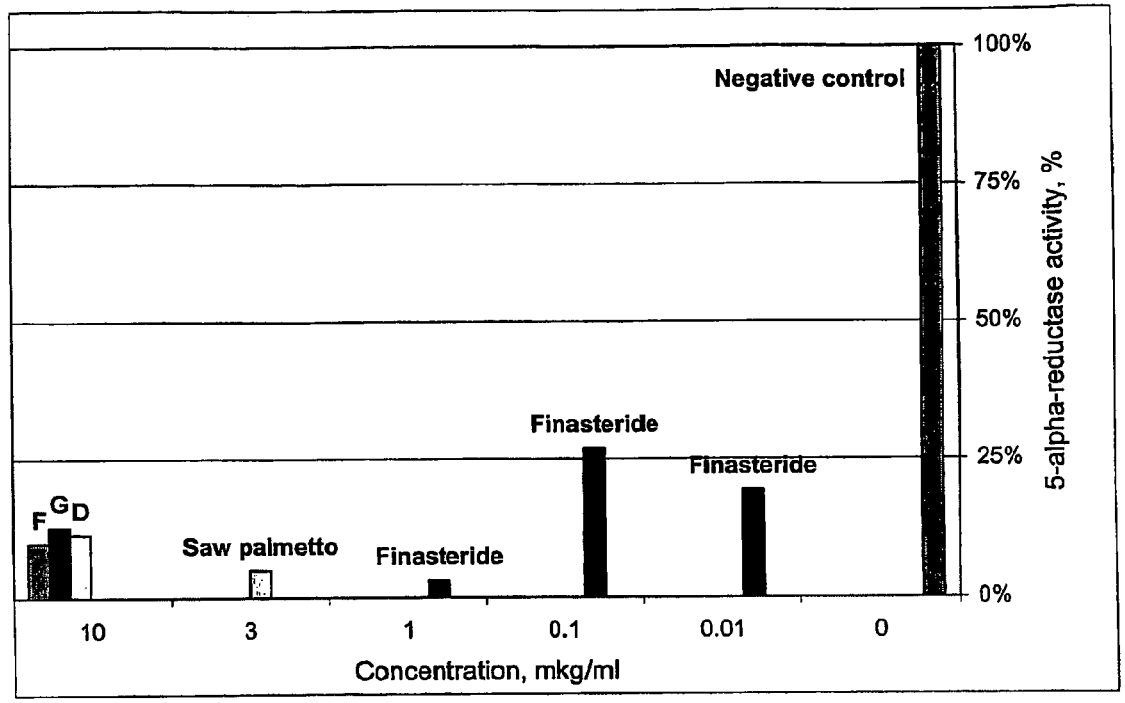
FIG. 3 is a bar graph depicting 5-alpha-reductase inhibition (%) in a human foreskin fibroblasts model, as induced by different concentrations of NABIA D, G and F fractions, compared to Finasteride, Saw Palmetto and no-inhibitor (negative control, 100%).

FIG. 3 is a bar graph depicting 5-alpha-reductase inhibition (%) in a human foreskin fibroblasts model, as induced by different concentrations of NABIA D, G and F fractions, compared to Finasteride, Saw Palmetto and no-inhibitor (negative control, 100%). As can be seen in FIG. 3, fractions D, F and G of the NABIA extract reduced the activity of the 5-alpha-reductase enzyme to about 10% of the original activity.

Example 5

Alpha-1-Adrenoreceptors Inhibition

Alpha-1 adrenoreceptors inhibition was measured for several extracts and fractions prepared according to Example 1 and compared to a synthetic alpha blocker and to a natural source commonly used to treat BPH, saw palmetto. The results are shown in Table 2 below.

TABLE 2

| Group | Synthetic products | Natural products | | |
|---|---|---|---|---|
| Name | Terazosin | Saw Palmetto | Fraction D | Fraction E |
| $IC_{50}$ | ~$10^2$ ng/ml | ~$3*10^{10}$ ng/ml | $10^3$ ng/ml | $5*10^4$ ng/ml |

Table 2 shows that while the saw palmetto, which is a commonly used natural product for the treatment of BPH, showed practically no alpha-1-blocking activity, the NABIA fractions D and F were significantly more active, by as much as 4-5 orders of magnitude. Similar results were obtained from the NABIA extract obtained according to the process of Example 2.

Table 3 below shows the alpha-1-blocker activity of various fractions and extracts.

TABLE 3

| | | | Results of test |
|---|---|---|---|
| # | Sample origin/history | Concentration | % Inhibition |
| 1 | NABIA of example 1 | 100 μg/ml | 53% |
| 2 | | 100 μg/ml | 69.8% |
| 3 | | 1 μg/ml | 3.8% |
| 4 | NABIA of Example 2 | 300 μg/ml | 68% |
| 5 | | 300 μg/ml | 55% |

Furthermore, it has been shown that the NABIA extract obtained according to Example 2 had alpha one selective activity for alpha 1A ($\alpha_{1A}$), 1B ($\alpha_{1B}$) and 1D ($\alpha_{1D}$) as can be seen in Table 4 below and in FIG. 4 which is a graph showing the alpha-1 specific inhibition of NABIA maltotextrine capsules and NABIA extracts over a period of three months.

TABLE 4

| | % Inhibition relative to control Specific Binding | | |
|---|---|---|---|
| Concentration | $\alpha_{1A}$ control = WB 4101 | $\alpha_{1B}$ | $\alpha_{1D}$ control = prazosin |
| 300 μg/ml | 89% | 87% | 80% |
| 50 μg/ml | 99% | 99% | 103% |

Figure 4:
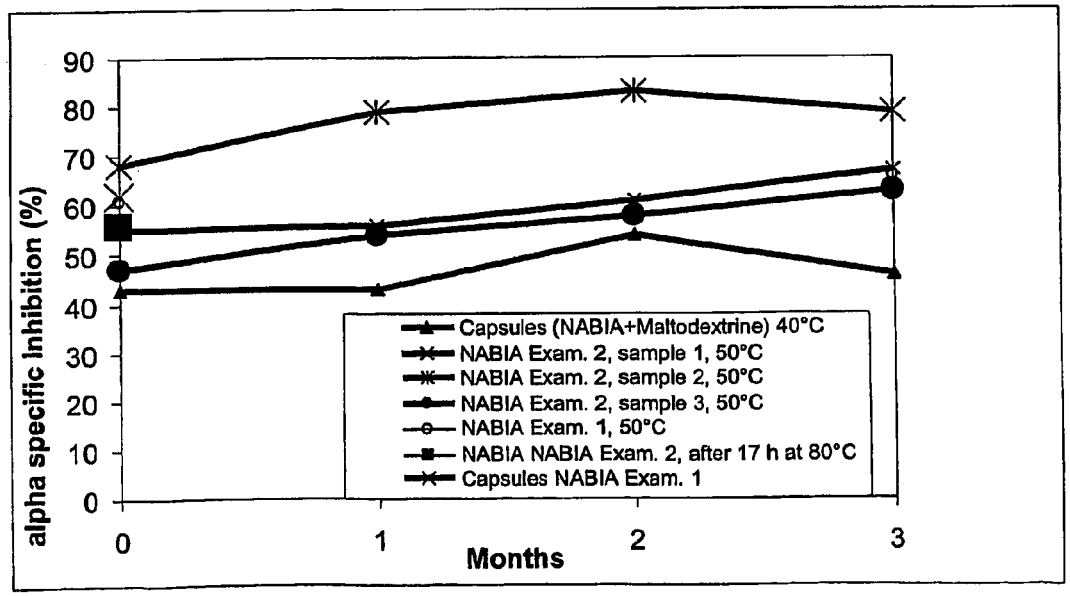
FIG. 4 is a graph showing the alpha-1 specific inhibition of NABIA maltotextrine capsules and NABIA extracts over a period of three months.

Furthermore, the biological alpha 1 inhibition was not affected under the conditions of accelerated stability study according to pharmacopeias standards, as can be seen in FIG. 4.

In Vivo Experiments

Materials and Experimental Methods:

Toxicology was done in Harlan Biotech Israel Ltd., which is GLP certified according to directive 88/320/EEC in toxicity studies.

Alfuzosin, a standard a blocker for BPH treatment, was obtained from Sanofi-Aventis.

Permixon, a natural extract for BPH treatment, was obtained from Pierre Fabre Medicament.

International prostate symptom score (IPSS) is defined in http://www.cpcn.org/ipss.pdf and ranges from 0 to 35 points.

Qmax is defined as the peak urine flow rate (ml/sec).

Clinical trials—The short-term efficacy of NABIA was assessed after 16 weeks in a double blind placebo controlled clinical study was performed on 15 patients having lower urinary tract symptoms (LUTS) caused by Benign Prostatic Hyperplasia (BPH). The study was conducted in the Zfat Hospital in Israel under the supervision of Dr Oscar Kotliroff, Head of the Department of Urology (principal investigator). Patients were chosen to include men with diagnosed BPH according to table 6 below:

TABLE 6

| Parameter | Threshold |
|---|---|
| History | Over 1 year history of LUTS (irritative or obstructive) |
| Age | Over 50 years |
| Digital Rectal Examination (DRE) | Benign appearance prostate gland; degree of enlargement depending on compound |
| I-PSS (0 to 35) | Over 7 points, depending on situation |
| $Q_{max}$ | <15 ml/second, |

Subjective and objective clinical variables were assessed using the International Prostate Symptom Score (IPSS), peak urinary flow rate ($Q_{max}$), average flow rate (Qavg) and flow time/void time. The study results were compared to "Meta-analysis of clinical trials of serenoa repens" (Boyle, 2004) that includes commonly used synthetic drugs: Finasteride, as a Gold standard of 5-α reductase for BPH treatment, Alfuzosin, as a Gold standard of alpha blockers for BPH treatment, and Permixon, as a Gold standard of natural extract for BPH treatment.

The patients received a starting dose of NABIA of 250 mg/day (one 250 mg capsule), for 6 weeks increased to 500 mg/day from week 7 to week 16 (two 250 mg capsules per day).

Example 6

Toxicological Results

Acute Oral Toxicity Acute Toxic Class Method in rats was done for fractions: NABIA-E, NABIA-G and for the natural combination thereof (NABIA) in concentrations of 300 mg/kg, 2000 mg/kg and 5000 mg/kg.

The mammal toxicity studies showed that none of the NABIA fractions, nor the combination thereof, produced any toxicity even at the high doses (5000 mg/kg).

General pathology observation carried out for relevant organs including liver and skin had no abnormality. Histopathology of liver was assessed with no special findings.

Example 7

Results of a NABIA Clinical Trial

All clinical variables showed significant sustained improvements over baseline throughout the study period in 75% of the patients treated with NABIA. Furthermore, the NABIA was found to be well tolerated: comprehensive physician checkup and laboratory testing observed no adverse effects of any kind the trial period in human clinical trials.

The invention claimed is:

1. A water-soluble alcoholic extract of *Opuntia ficus-indica* flower (NABIA extract), a component thereof (NABIA fraction) or any mixture of components thereof, which is substantially free of non water-soluble residues, and exhibits an effective alpha-1-adrenergic receptor blocking activity, wherein said extract forms a clear solution in water upon adding 50 ml of water to a sample of 50 grams of the extract, mixing them for at least 2 hours at room temperature, and observing the obtained solution 24 hours from beginning of mixing, and wherein the water-soluble alcoholic extract is obtained from a process that includes heating a mixture comprising water and at least one organic soluble material extracted from an *Opuntia ficus-indica* flower.

2. The NABIA extract of claim 1 being characterized by a half maximal alpha-1-blocker inhibitory concentration (alpha-1 IC50) which is lower than $10^6$ ng/ml.

3. The NABIA extract of claim 1, exhibiting a selective alpha-1 blocking activity for any of alpha-1A ($\alpha$1A), alpha-1B ($\alpha$1B), alpha-1D ($\alpha$1D) adrenergic receptor.

4. The NABIA extract of claim 1, further exhibiting a 5-alpha-reductase inhibition activity.

5. A formulation comprising the NABIA extract of claim 1, and a pharmaceutically acceptable carrier.

6. The formulation comprising of claim 5, wherein said carrier is a solid carrier.

7. The formulation of claim 6 wherein said solid carrier is selected from the group comprising of maltodextrin, dextrins, silicon dioxide, starches, gums and hydrocolloids.

8. The formulation of claim 5 further comprising at least one pharmaceutically acceptable additive and/or at least one phytotherapeutic acceptable additive.

9. The NABIA extract of claim 1 being packaged in a packaging material and identified in print, in or on said packaging material, for use in the treatment of a Urinary Tract Disorder (UTD), and/or for use in treatment of a Urinary Tract Disorder (UTD), and/or for use in inhibiting non-selective-alpha-1-adrenergic receptor activity and/or for use in a selective inhibition of any of alpha-1A ($\alpha$1A), alpha-1B ($\alpha$1B), alpha-1D ($\alpha$1D) adrenergic receptor, and/or for use inhibiting 5-alpha-reductase enzymatic activity.

10. The NABIA extract of claim 1, further comprising a therapeutically active agent and/or phytotherapeutic active agent.

11. A method of treating a Urinary Tract Disorder (UTD), the method comprising administering to a subject in need thereof a therapeutically effective amount of NABIA extract of claim 1, thereby treating said UTD.

12. The method of claim 11 wherein said UTD is selected from the group consisting of lower urinary tract syndrome (LUTS) and benign prostatic hyperplasia (BPH).

13. A method for inhibiting alpha-1-adrenergic receptor activity, the method comprising administered to a subject in need thereof a therapeutically effective amount of the NABIA extract of claim 1, thereby inhibiting said alpha-1-adrenergic receptor activity.

14. A method for selectively inhibiting any of alpha-1A ($\alpha$1A), alpha-1B ($\alpha$1B), alpha-1D ($\alpha$1D) adrenergic receptor activity, the method comprising administering to a subject in need thereof a therapeutically effective amount of the NABIA extract of claim 1, thereby specifically inhibiting any of alpha-1A ($\alpha$1A), alpha-1B ($\alpha$1B), alpha-1D ($\alpha$1D) adrenergic receptor activities.

15. A method for inhibiting both alpha-1 adrenergic receptor activity and 5-alpha-reductase enzymatic activity, the method comprising administering to a subject in need thereof a therapeutically effective amount of the NABIA extract of claim 1, thereby inhibiting said alpha-1-adrenergic receptor activity and said 5-alpha-reductase enzymatic activity.

16. The method of claim 11, wherein said subject is a human subject, and wherein said formulation or said NABIA extract is administered at a daily dose of between 3.0 mg extract/day to about 1000 mg extract/day.

17. A process for preparing the water-soluble alcoholic extract of *Opuntia ficus-indica* flower of claim 1 (NABIA extract), said process comprising;
   a) obtaining naturally dry *Opuntia ficus-indica* (OFI) flowers;
   b) crushing and grinding said OFI flowers to obtain an OFI flower powder;
   c) extracting said powder in an alcoholic solvent at room temperature to obtain a primary extract solution containing a primary extract and exhausted flower;
   d) separating said exhausted flower from said primary extract;
   e) evaporating said alcoholic solvent from said primary extract solution to obtain a secondary extract;
   f) adding water to said secondary extract;
   g) heating to above 80° C.;
   h) depositing any non water-soluble residues from said secondary extract, wherein said depositing is conducted under overnight cooling; and
   i) separating said non water-soluble residues from said secondary extract to obtain a clear water-soluble alcoholic extract of the *Opuntia ficus-indica* flower, which is substantially free of any non water-soluble residues (NABIA extract).

18. A process for preparing the formulation of claim 5, said process comprising adding a carrier to the NABIA extract.

19. The process of claim 18, further comprising adding at least one pharmaceutically acceptable additive and/or at least one therapeutically active agent and/or at least one phytotherapeutic active agent.

* * * * *